US008064986B2

(12) United States Patent
Profio et al.

(10) Patent No.: US 8,064,986 B2
(45) Date of Patent: Nov. 22, 2011

(54) METHOD AND SYSTEM FOR DISPLAYING A CINE LOOP FORMED FROM COMBINED 4D VOLUMES

(75) Inventors: Mark Vincent Profio, Elm Grove, WI (US); Darin Okerlund, Muskego, WI (US); Karen Procknow, Willowbrook, IL (US); Ann Christine Hole, Greenville, OH (US)

(73) Assignee: General Electric Company, Schenectady, NY (US)

( * ) Notice: Subject to any disclaimer, the term of this patent is extended or adjusted under 35 U.S.C. 154(b) by 654 days.

(21) Appl. No.: 11/286,833

(22) Filed: Nov. 23, 2005

(65) Prior Publication Data
US 2007/0129627 A1 Jun. 7, 2007

(51) Int. Cl.
*A61B 5/05* (2006.01)
(52) U.S. Cl. .................. 600/425; 382/128; 345/633
(58) Field of Classification Search .......... 600/410, 600/419, 425, 436, 454, 465, 504; 345/419, 345/427, 629, 633, 473, 1.3; 382/128
See application file for complete search history.

(56) References Cited

U.S. PATENT DOCUMENTS

| 6,980,844 | B2 | 12/2005 | Schoisswohl |
| 7,020,511 | B2 | 3/2006 | Boyd et al. |
| 2003/0105605 | A1 | 6/2003 | Degani et al. |
| 2004/0027359 | A1* | 2/2004 | Aharon et al. ............... 345/619 |
| 2004/0047497 | A1* | 3/2004 | Daw et al. ................... 382/128 |
| 2004/0081269 | A1* | 4/2004 | Pan et al. ........................ 378/4 |
| 2004/0096088 | A1* | 5/2004 | Kohle ........................... 382/128 |
| 2005/0285858 | A1 | 12/2005 | Yang et al. |
| 2006/0079743 | A1 | 4/2006 | Ferrant et al. |

OTHER PUBLICATIONS

Zhang et al. Visualization and Post-processing of 5D Brain Images. Proceedings of the 2005 IEEE. p. 1083-1086. Sep. 2005.*
Narayanan et al. Improved Image Quality and Computation Reduction in 4-D Reconstruciton of Cardiac-Gated SPECT Images. IEEE Transactions on Medical Imaging. 19(5):p. 423-433. May 2000.*

* cited by examiner

*Primary Examiner* — Parikha Mehta
(74) *Attorney, Agent, or Firm* — Dean D. Smail; The Small Patent Law Group

(57) ABSTRACT

Methods and systems for displaying medical images are provided. The method includes performing three-dimensional (3D) volume visualization on a plurality of two-dimensional (2D) images acquired continuously. The method further includes combining the 3D volume visualizations to form a plurality of four-dimensional (4D) volumes representing the 3D volume visualizations over a period of time and displaying at least one 4D volume.

17 Claims, 6 Drawing Sheets

METHOD AND SYSTEM FOR DISPLAYING A CINE LOOP FORMED FROM COMBINED 4D VOLUMES

BACKGROUND OF THE INVENTION

This invention relates generally to medical imaging systems, and more particularly, to systems that display images resulting from scans performed by medical imaging systems.

Medical analysis and diagnosis is often performed with medical imaging system having displays to display the results of a scan of a patient. Analysis of the images can be very time sensitive or critical with added time possibly resulting in increased risk to the patient due to the patient condition. This added time can result in increased risk of permanent injury or death. For example, a brain attack is a time critical patient condition where every minute counts. Accordingly, rapidly determining the appropriate diagnosis and treatment path is often critical and can reduce the chances of permanent injury or death. In particular, for a patient showing signs of a possible stroke, it is important to quickly determine whether there is brain hemorrhaging. Increased time in diagnosis can increase the likelihood of permanent injury. If the diagnosis is not correct, for example, if there is no stroke and a patient is given a stroke treatment, serious harm and death can result. Improper diagnosis can lead to improper treatment. Thus, fast and robust diagnosis and appropriate patient treatment helps to ensure improved patient outcomes.

Known methods for displaying medical image data to analyze for diagnosing a patient can be difficult to view or navigate, thereby increasing the time for diagnosis. For example, due to the basic complexity of some anatomical regions, such as the brain, existing segmentation techniques do not allow for a clean visualization. Similarly, these systems display a single image in time and may not provide the clinician with all of the information needed for a proper diagnosis. The clinician often has to view different images, which may be on different screens or may not be able to be viewed simultaneously. This increases the difficulty in reviewing and analyzing the images, thereby increasing the time for a proper diagnosis.

Thus, known methods and systems for displaying medical images can be difficult to navigate and review. Further, these system can be cumbersome or awkward to use, further adding time before a proper diagnosis. This added time can result in serious consequences.

BRIEF DESCRIPTION OF THE INVENTION

In accordance with one embodiment, a method for displaying medical image data is provided. The method includes performing three-dimensional (3D) volume visualization on a plurality of two-dimensional (2D) images acquired continuously. The method further includes combining the 3D volume visualizations to form a plurality of four-dimensional (4D) volumes representing the 3D volume visualizations over a period of time and displaying at least one 4D volume.

In accordance with another embodiment, a method for tracking blood flow through an organ is provided. The method includes combining acquired scan images of an organ to form three-dimensional (3D) visualizations of the organ. The method further includes forming a plurality of four-dimensional (4D) volumes from the 3D volume visualizations. The 4D volumes represent the 3D volume visualizations over a period of time and show blood flow through the organ.

In accordance with yet another embodiment, a medical imaging system is provided that includes a scanner configured to continuously acquire image data sets. The medical imaging system further includes a four-dimensional (4D) processor configured to combine reconstructed three-dimensional (3D) volume visualizations of the acquired image data sets to form 4D volumes representing the 3D volume visualizations over a period of time. The medical imaging system also includes a 4D viewer configured to display the 4D volumes and receive user inputs.

DETAILED DESCRIPTION OF THE INVENTION

Figure 1:
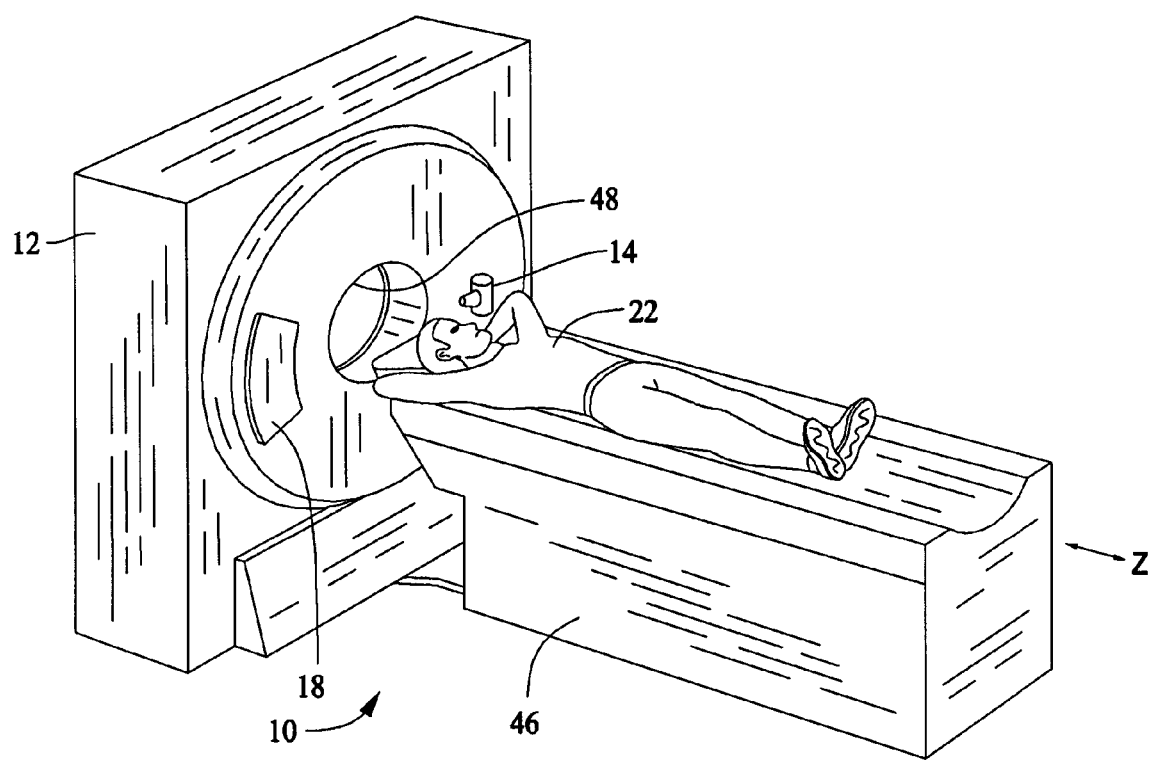
FIG. 1 is a perspective view of an exemplary imaging system operated in accordance with an embodiment of the invention.
Figure 2:
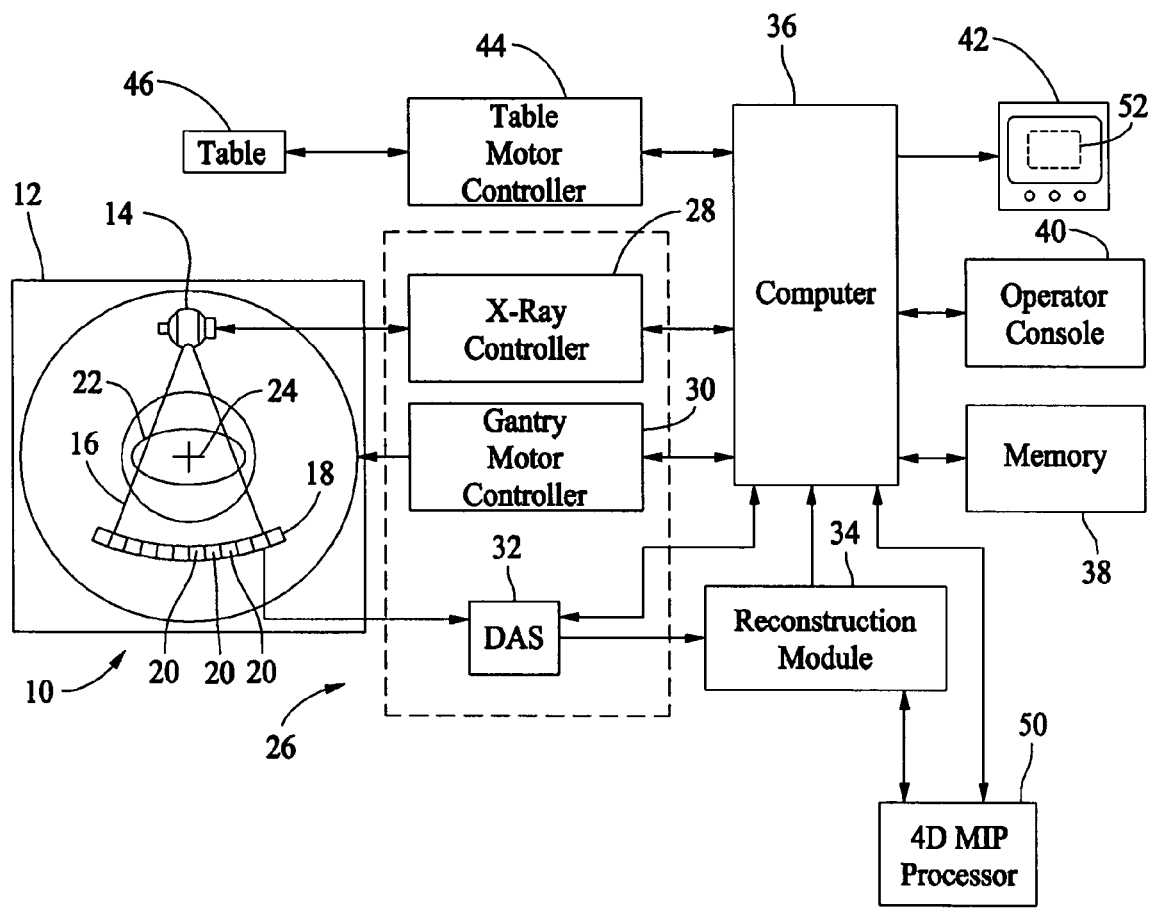
FIG. 2 illustrates a block diagram of the imaging system illustrated in FIG. 1.

FIG. 1 is a perspective view of an exemplary imaging system 10. FIG. 2 is a schematic block diagram of the imaging system 10 (shown in FIG. 1). In an exemplary embodiment, the imaging system 10 is a single modality imaging system, for example, a computed tomography (CT) system. However, it should be understood that the various embodiments may be implemented in connection with imaging systems having more than one imaging modality (i.e., multi-modality imaging systems). Additionally, although the various embodiments may be described in connection with a particular imaging modality, for example, CT imaging, different imaging modalities both medical and non-medical may be used, for example, Positron Emission Tomography (PET), and in general any type of x-ray or nuclear imaging.

Referring now specifically to FIGS. 1 and 2, a computed tomography (CT) imaging system 10 is shown that includes a gantry 12 for a CT scanner. The gantry 12 includes an x-ray source 14 that projects a beam of x-rays 16 toward a detector array 18 on the opposite side of the gantry 12. The detector array 18 is formed by detector elements 20 (e.g., a plurality of detector rows) that together sense the projected x-rays that pass through an object 22, for example a medical patient. The detector array 18 may be fabricated in a single slice or multi-slice configuration. Each detector element 20 produces an electrical signal that represents the intensity of an impinging x-ray beam and hence the attenuation of the beam as the beam passes through the object 22. During a scan to acquire x-ray projection data, the gantry 12 and the components mounted thereon rotate about a center of rotation 24, which may define an examination axis.

The rotation of the gantry 12 and the operation of the x-ray source 14 are controlled by a control mechanism 26 of the imaging system 10, which in one embodiment is a CT imaging system. The control mechanism 26, in an exemplary embodiment, includes an x-ray controller 28 that provides power and timing signals to the x-ray source 14 and a gantry motor controller 30 that controls the rotational speed and position of the gantry 12. A data acquisition system (DAS) 32 of the control mechanism 26 samples data (e.g., analog data) from the detector elements 20 and converts (or conditions) the data to digital signals for subsequent processing. The DAS 32 outputs projection data sets including attenuation measurements obtained at particular gantry rotation angles, for example, from a low dose mode CT scan. A group of projection data sets form a complete scan of object 22. A reconstruction module 34 receives sampled and digitized x-ray data from the DAS 32 and performs image reconstruction as explained below. The reconstruction data sets output by the reconstruction module 34 are provided as an input to a computer 36 or other processing unit that stores the reconstruction data sets in a memory 38. The reconstruction data sets may represent volumetric data sets and/or image slices through the object 22. The computer 36 also receives commands and scanning parameters from an operator via an operator console 40 that may include one or more use inputs, for example, a keyboard (not shown). An associated display, for example, a cathode ray tube display 42 allows the operator to observe reconstructed image and other data from the computer 36. Further, the operator supplied commands and parameters are used by the computer 36 to provide control signals and information to the DAS 32, the x-ray controller 28 and the gantry motor controller 30. In addition, the computer 36 operates a table motor controller 44 that controls a motorized table 46 to position the object 22 in the gantry 12. In particular, the table 46 moves portions of the object 22 through a gantry opening 48.

In one embodiment, the computer 36 includes a read/write device (not shown), for example, a floppy disk drive, CD-ROM drive, DVD drive, magnetic optical disk (MOD) device, or any other digital device including a network connecting device such as an Ethernet device for reading instructions and/or data from a computer-readable medium, such as a floppy disk, a CD-ROM, a DVD or an other digital source such as a network or the Internet, as well as yet to be developed digital means. In another embodiment, the computer 36 executes instructions stored in firmware (not shown). The computer 36 is programmed to perform functions as described herein, and as used herein, the term computer is not limited to integrated circuits referred to in the art as computers, but broadly refers to computers, processors, microcontrollers, microcomputers, programmable logic controllers, application specific integrated circuits, and other programmable circuits, and these terms are used interchangeably herein.

The imaging system 10 also includes a four-dimensional Maximum Intensity Projection (4D MIP) processor 50 communicatively coupled to the reconstruction module 34 and the computer 36. The 4D MIP processor 50 is configured to process received image data from the CT scanner or reconstructed image data from the reconstruction module 34 to form time dependent image data for display on a 4D MIP viewer 52 as described in more detail below. The 4D MIP viewer 52 may be provided on a portion or all of the display 42. Although the 4D MIP processor 50 is illustrated as a separate component, it should be understood that that functions performed by the 4D MIP processor 50 may be incorporated into functions performed by, for example the computer 36. Accordingly the 4D MIP processor 50 may be embodied in a software code segment executing on a multifunctional processor or may embodied in a combination of hardware and software.

Additionally, although described in a medical setting, it is contemplated that the embodiments of the invention may be implemented in connection with other imaging systems including industrial imaging systems such as, for example, a baggage scanning CT system typically used in a transportation center, for example, an airport or a rail station.

Figure 3:
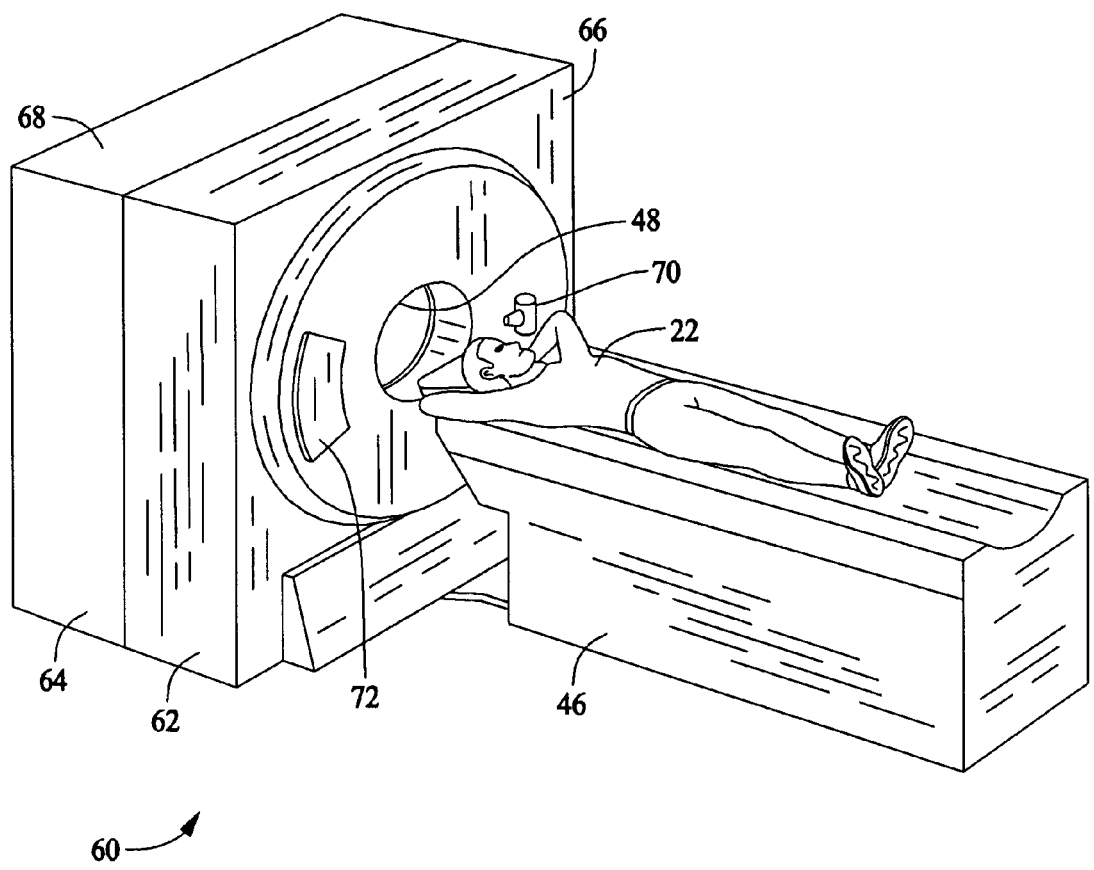
FIG. 3 is a perspective view of another exemplary imaging system operated in accordance with an embodiment of the invention.

Further, although the imaging system is described providing a single imaging modality, a multi-modality imaging system 60 may be provided as shown in FIG. 3 (wherein similar reference numerals to FIG. 1 represent like components). The imaging system 60 is a multi-modal imaging system and includes a first modality unit 62 and a second modality unit 64. The modality units 62 and 64 enable the imaging system 60 to scan an object, for example, a patient, in a first modality using the first modality unit 62 and to scan the object in a second modality using the second modality unit 64. The imaging system 60 allows for multiple scans in different modalities to facilitate an increased diagnostic capability over single modality systems. In one embodiment, the multi-modality imaging system 60 is a Computed Tomography/Positron Emission Tomography (CT/PET) imaging system. The CT/PET system includes a first gantry 66 associated with the first modality unit 62 and a second gantry 68 associated with the second modality unit 64. In alternative embodiments, modalities other than CT and PET may be employed with the imaging system 60. The first gantry 66 includes an x-ray source 70 that projects a beam of x-rays toward a detector array 72 on the opposite side of the gantry 66. The detector array 72 may formed by a plurality of detector rows (not shown) including a plurality of detector elements that together sense the projected x-rays that pass through an object, such as the patient 22. Each detector element produces an electrical signal that represents the intensity of an impinging x-ray beam and therefore, allows estimation of the attenuation of the beam as it passes through the object or patient 22. Further, a contrast agent may be used to provide additional information during scanning.

During a scan, to acquire x-ray projection data, the gantry 66 and the components mounted thereon rotate about an examination axis. FIG. 2 shows only a single row of detector elements 20 (i.e., a detector row). To acquire emission data, the gantry 68 rotates one or more gamma cameras (not shown) about the examination axis. The gantry 68 may be configured for continuous rotation during an imaging scan and/or for intermittent rotation between imaging frames. The rotation of gantries 66 and 68, and the operation of x-ray source 70 are controlled by a system similar to that shown in FIG. 2. However, the DAS 32 of the control mechanism 26 samples data from the detector elements and the gamma cameras and conditions the data for subsequent processing. The reconstruction module 34 receives sampled and digitized x-ray data and emission data from the DAS 32 and performs image reconstruction.

Figure 4:
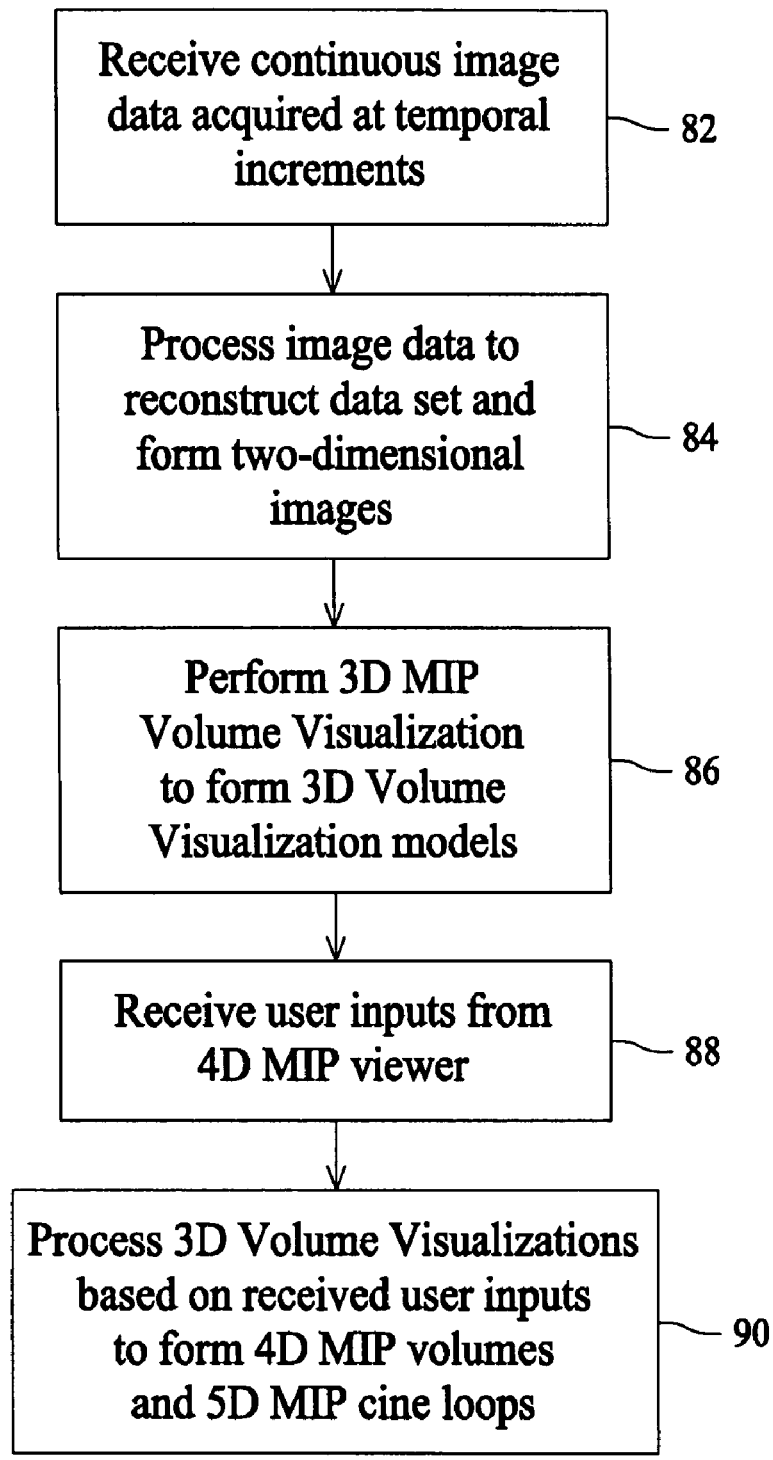
FIG. 4 is a flow chart of a method for displaying four-dimensional (4D) images in accordance with an embodiment of the invention.

Various embodiments provide processing of image data to form time dependent images for display. In one exemplary embodiment, by combining 3D MIP images, 4D MIP images may be formed and displayed in various and different configurations on a 4D MIP viewer. FIG. 4 is a flow chart setting forth an exemplary method 80 performed by the 4D MIP processor 50 (shown in FIG. 2) to generate 4D images for display on the 4D MIP viewer 52 (shown in FIG. 2). It should be noted that the method 80 may be modified and used in connection with scans of objects other than human bodies and with imaging systems other than medical imaging systems. Further, although reference may be made herein to imaging a particular object, for example, a human brain, the various embodiments and the method 80 may be used to image different objects, for example, to image other body parts and provide multiple time based imaging for other clinical applications.

Specifically, the method 80 illustrates a process for image data processing for use in connection with an imaging system, and more particularly a medical imaging system such as a CT and/or PET imaging system. In particular, at 82 continuous image data acquired at temporal increments from, for example, a CT or PET scanner, is received. For example, volumetric PET or CT image datasets are acquired in a continuous acquisition in any manner known in the art, and which may be for a desired anatomical location. The datasets are acquired at predetermined or defined temporal increments based on, for example, a desired overall patient scan time. For example, for a brain scan, a single continuous data acquisition for a scan time of thirty-five seconds may be performed over a defined coverage area, such as a forty millimeter (mm) coverage area. The scanner acquiring the image data rotates at a predetermined speed, for example one rotation per second and acquires a predetermined number of images, for example, sixty-four, in that rotation. Thus, thirty-five data sets of sixty four images are acquired continuously.

It should be noted that the number of images acquired, the scan area and the scan time can be modified as desired or needed. Further, it should be noted that the scan may be performed in different modes of operation, for example, in a low dose mode of operation for use in generating medical images for diagnosis.

The acquired data sets are processed at 84, and more particularly, reconstructed in any manner known in the art to form two-dimensional (2D) images. For example, multiple stacks of 2D flat images are formed. Using the same example as above, one data set per rotation of the scanner over thirty-five seconds results in thirty-five stacks or sets of sixty-four images every second or rotation and covering the 40 mm, which in a brain scan can encompass the Circle of Willis anatomy. Thus, image data reconstruction produces stacks of flat 2D images at defined temporal increments for the duration of the scan acquisition.

Thereafter, at 86, three-dimensional (3D) volume visualization is performed on the 2D stacks of images to form 3D volume visualization models. In particular, maximum intensity pixel projection is performed through each stack of 2D images resulting in a 3D MIP volume at each point in time. Further, 3D MIP volume visualization is applied to each of the discrete 2D flat image stacks, with each stack representing a defined point in time during the acquisition and consequently, for example, a defined point in a vascular cycle that may be highlighted and identified with IV contrast enhancement or PET imaging as is known in the art. Thereafter, user inputs from the 4D MIP viewer are received at 88, which may define different parameters for subsequent combination of the 3D MIP images, for example, the type of combining (such as digital addition or subtraction), weighting, averaging, slice width, slice angle through the volume, volume rendering etc. Using one or more received user inputs, the 3D volume visualizations are processed to create 4D MIP volumes and 5D MIP cine loops (4D MIP images chained together and sequenced through time) at 90. For example, the 4D MIP viewer allows users to create 4D MIP volumes from 2 to N 3D MIP volume visualizations by combining two or more 3D MIP volume visualizations. Combination of the 3D MIP volume visualizations can be accomplished with a variety of techniques including MIP, digital addition and subtraction, weighting, averaging, minimum MIP, volume rendering, and other mathematical constructs. The 4D MIP visualizations can then be viewed temporally in time, viewed by spatial location, re-combined with digital addition and subtraction, MIP, weighting, average, minimum MIP, volume rendering, and other mathematical constructs to provide for display, for example, images showing different phases of vascular blood flow and other diagnostic information. It should be noted that 1 to N time based volume data sets may be digitally added or subtracted.

These resulting 4D MIP volume visualizations then can be arithmetically modified or combined, for example, by scrolling through time, scrolling through spatial location, or slicing through the volume at different angles and combined or scripted together to form a 5D cine loop or movie, which may, for example, provide a continuous replaying of the 4D MIP volume visualizations over a vascular cycle. For example, in blood flow type studies, one time and space MIP'ed visualization may be digitally subtracted from another time and space MIP'ed visualization at two different points in time. One intermediate visualization also may be centered, for example, about a time sample ten within a time window of five (i.e., a MIP over time samples eight through twelve). A second intermediate visualization may then be centered at time sample four (i.e., a MIP over time samples two through six). Digital subtraction may then be performed subtracting the second intermediate visualization from the first, representing the average blood flow between time sample four and time sample ten. It should be noted that with respect to combing image data sets, a slab or slice window in time may be established, with the specification of maximum, average or MIP, and a time window less than N can provide special cut line in the image data sets.

Figure 5:
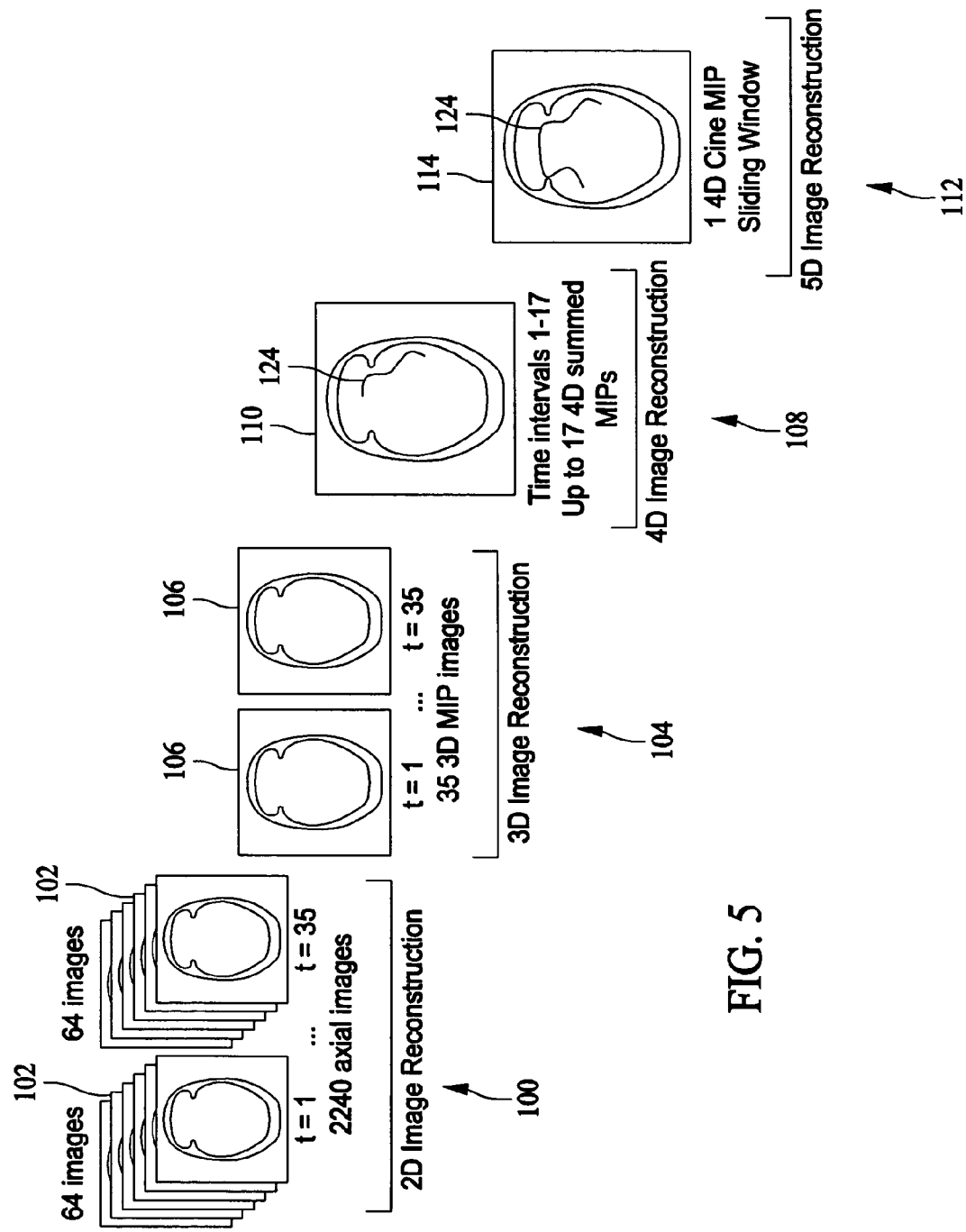
FIG. 5 is a diagram illustrating the different processes of the method shown in FIG. 4 for combing different image sets.

Thus, as shown in FIG. 5, 2D image reconstruction may be performed during a first processing step 100 wherein a series of 2D image stacks 102 (e.g., sixty-four images in each of thirty-five stacks) are formed. Thereafter, during a second processing step 104, 3D image reconstruction is performed to generate a series of 3D MIP images 106 (e.g., thirty-five MIP images). Subsequently, in a third processing step 108, two or more 3D MIP images, for example, adjacent or neighboring images are combined to form a plurality of 4D MIP images 110, which may be, for example, 4D summed MIP images (e.g., up to seventeen images). The formation of the 4D MIP images may be based on one or more user inputs. Finally, in a fifth processing step 112, a 5D cine MIP 114 is formed by combining the 4D MIP images. Thus, as shown in the 4D MIP images 110 and the 5D cine MIP 114 blood flow 124 through an organ, such as the brain, may be displayed.

Figure 6:
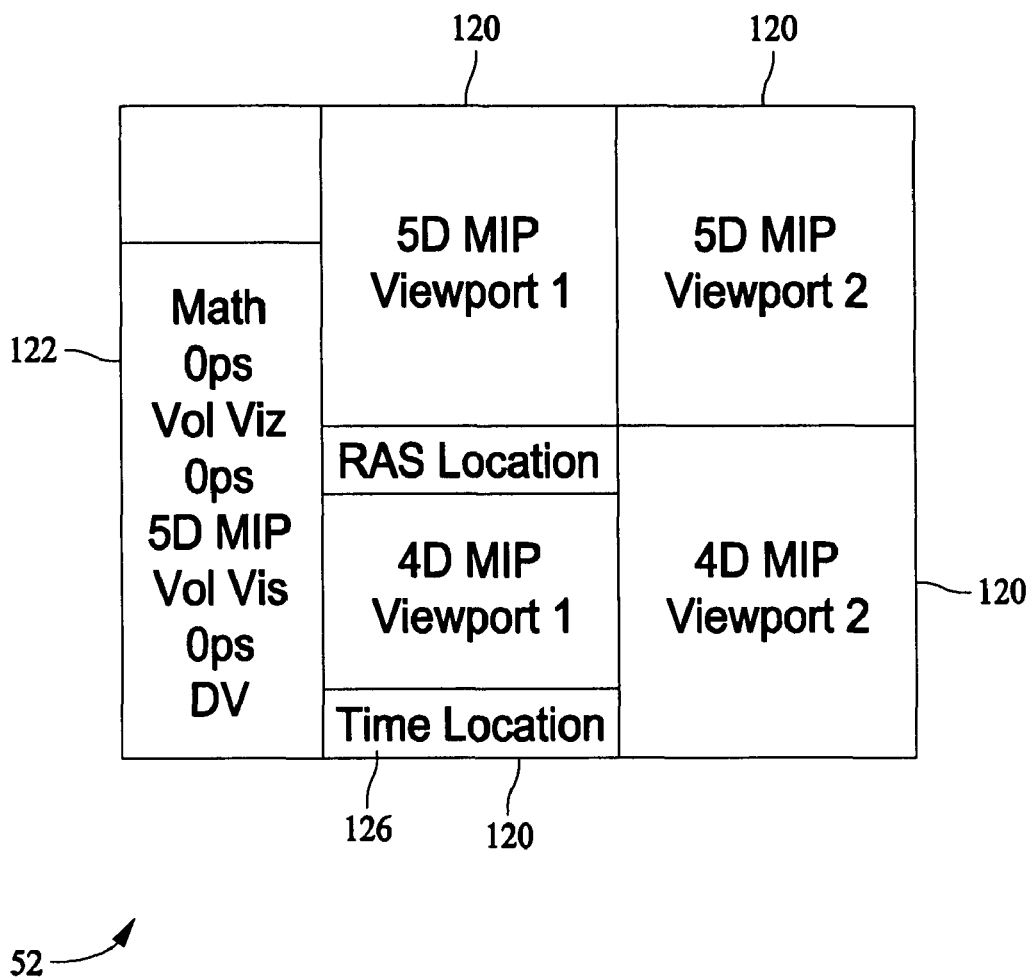
FIG. 6 is a block diagram of an exemplary 4D viewer constructed in accordance with an embodiment of the invention.

A display, for example, the 4D MIP viewer 52 as shown more particularly in FIG. 6, may include a plurality of viewports 120 segmenting the display. For example, two viewports 120 may be provided for displaying 4D MIP images and two viewports 120 may be provided for displaying 5D cine MIPs. A user interface portion 122 also may be provided to allow receiving user inputs, etc. as described in more detail herein. A user may be provided with a scroll bar 126 to display a particular image at a particular point in time or spatial location, for example, to view blood flow at a particular point in the blood flow cycle. A user viewing the 4D MIP viewer 52 can simultaneously view multiple sets of images at multiple points in time. For example, a user can view or track blood flow in a brain through all three phases. This time based viewing may be provided manually using a scroll bar or provided automatically by viewing the processed 4D MIP images as a 5D cine loop.

The method 80 provides for temporal window compressing one to N points in time. If temporal windows are greater than a predetermined maximum, then the image may be averaged. For example, averaging may be used for low dose CT scanning modes, such as, for CT perfusion studies.

Other operations may be performed as part of the method 80. For example, auto-detection may be performed for the point in time with the greatest overall opacification of vessels allowing a user to position a window around this point in time. Auto-Detection of maximum opacification may be accomplished with a variety of methods including detection of a preset maximum Hounesfield Unit enhancement threshold, analyzing the first derivative of the slope of the enhancement curve versus time and detecting where the slope changes from positive to zero to negative, among other methods. Further, 4D temporal interactive capabilities within the volume visualization may be provided, for example, a virtual temporal and/or location slide bar on the 4D MIP viewer. A weighted MIP mode also may be provided wherein the most recent time point data has a greater weight than all the previous points, similar to spatial volume rendering. Another process may be provided that includes using a pre-contrast volume data set baseline with digital subtraction of the baseline volume from any other time based volume data set. Still another process may be provided to support interactive manipulation of the width of each 4D or 5D time slab, manipulation of the width of the 4D or 5D spatial slab, and navigation through the 4D and 5D volumes at different view angles. This provides, for example, a display of neuro vasculature at one or more blood flow phases including arterial, medial and venial.

It should be noted that up-front temporal processing may be performed to generate an intermediate 3D data set for volume visualization. This up-front processing can be performed temporally and then spatially, and may also be performed spatially and then temporally. Further, it should be noted that the combination of the image data sets, for example, the manner in which the data sets are digitally added or subtracted and the sequence for such operations may be determined based on clinical trials, which may then define a protocol.

Although various embodiments are described above relative to a particular medical imaging modality, various medical imaging modalities, such as computed tomography (CT), single positron emission tomography (SPECT), positron emission tomography (PET), nuclear magnetic resonance imaging (MRI), static X-ray imaging, dynamic (Fluoroscopy) X-ray imaging, and multimodality combinations thereof may also benefit from the methods described herein. Also, the use of various embodiments of the present invention is contemplated with respect to these modalities Exemplary embodiments of medical imaging systems and apparatus are described above in detail. The medical imaging system components illustrated are not limited to the specific embodiments described herein, but rather, components of each system may be utilized independently and separately from other components described herein. For example, the medical imaging system components described above may also be used in combination with different medical imaging system components.

A technical effect of the various embodiments of the systems and methods described herein include allowing viewing of multiple image data sets at multiple points in time.

Thus, the various embodiments provide a method for displaying time dependent information on a screen, thus allowing a clinician to perform analysis using a single display environment rather than sorting through multiple datasets independently. For example, clinical Neurological-Radiologist users may better visualize Circle of Willis (CoW) vasculature utilizing CT and PET imaging of the brain. These users can view a 3D visualization of CoW vasculature at different points in time that relate to phases of blood flow through the brain's vascular system. Thus, users can create vascular 3D visualizations of the brain's vascular system at these selected phases/time points to aid diagnosis and assessment of, for example, stroke or brain attack patients.

While the invention has been described in terms of various specific embodiments, those skilled in the art will recognize that the invention can be practiced with modification within the spirit and scope of the claims.

What is claimed is:

1. A method for displaying medical image data, said method comprising:
generating three-dimensional (3D) volume visualizations for a common region from a plurality of two-dimensional (2D) images acquired continuously over a volume-of-interest (VOI) that includes an entirety of the common region;
digitally combining the 3D volume visualizations to form a plurality of four-dimensional (4D) volume visualizations representing the 3D volume visualizations over a period of time, the plurality of 4D volume visualizations including first and second 4D volume visualizations, the first 4D volume visualization including the entirety of the common region during a first time period and the second 4D volume visualization including the entirety of the common region during a different second time period;
digitally combining the first and second 4D volume visualizations by digitally processing the first and second 4D volume visualizations to generate a modified 4D volume visualization of the entirety of the common region; and
displaying the modified 4D volume visualization on a display,
wherein the 3D volume visualizations comprise 3D Maximum Intensity Projection (MIP) volume representations, and the 4D volume visualizations comprise 4D MIP visualizations.

2. A method in accordance with claim 1 wherein the plurality of 2D images comprise one of computed tomography (CT) and positron emission tomography (PET) images.

3. A method in accordance with claim 1 wherein the displaying includes displaying the first and second 4D volume visualizations simultaneously on a single display, the method further comprising receiving user inputs for selecting the first and second 4D volume visualizations from the first and second time periods to be digitally combined.

4. A method in accordance with claim 1 further comprising receiving at least one user input and combining the 3D volume visualizations based at least in part on the at least one user input.

5. A method in accordance with claim 1 wherein the plurality of 2D images comprise images of a brain and the modified 4D volume visualization shows at least one blood flow phase of the brain vascular cycle.

6. A method in accordance with claim 1 further comprising providing a user operable input to view a 4D volume visualization at a point in time.

7. A method in accordance with claim 1 wherein the first and second 4D volume visualizations from the first and second time periods include a pre-contrast volume data set baseline and a volume data set showing a contrast agent, respectively.

8. A method in accordance with claim 1 further comprising defining a time interval for the 3D volume visualizations.

9. A method in accordance with claim 1 wherein the digitally combining includes at least one of weighting, averaging, volume rendering, digitally adding, and digitally subtracting the first and second 4D volume visualizations from the first and second time periods.

10. A method in accordance with claim 1 wherein the modified 4D volume visualization represents a 4D volume visualization between the first and second time periods.

11. A method in accordance with claim 1 wherein the modified 4D volume visualization represents a third 4D volume visualization during a predetermined diagnostic phase.

12. A method in accordance with claim 1 further comprising receiving user inputs for selecting the first and second 4D volume visualizations from the first and second time periods to be combined, the user inputs adjusting a length of the first or second time periods.

13. A method for tracking blood flow through an organ, said method comprising:
digitally combining acquired scan images of an organ to form three-dimensional (3D) visualizations of the organ, the organ including a common region;
forming four-dimensional (4D) volume visualizations form the 3D volume visualizations, the 4D volume visualizations representing the 3D volume visualizations over a period of time and showing blood flow through the common region of the organ, the 4D volume visualizations including first and second 4D volume visualizations, the first 4D volume visualization including an entirety of the common region during a first period and the second 4D volume visualization including the entirety of the common region during a different second time period;
digitally combining the first and second 4D volume visualizations by digitally processing the first and second 4D volume visualizations to form a modified 4D volume visualization of the entirety of the common region; and
displaying the modified 4D volume visualization on a display,
wherein the 3D visualizations and 4D visualizations comprise Maximum Intensity Projection (MIP) information.

14. A method in accordance with claim 13 further comprising tracking the blood flow based on a flow of a contrast agent injected into the organ and displaying the tracked blood flow.

15. A method in accordance with claim 13 wherein the 4D volume visualizations comprise volume images of one or more blood flow phases of the brain vascular cycle, the method further comprising tracking blood flow during at least one of an arterial phase, a medial phase, and a venial phase of the brain vascular cycle using the 4D volume visualizations and displaying the tracked blood flow.

16. A method in accordance with claim 13 further comprising using images from a positron emission tomography (PET) scan to form the 4D volume visualizations.

17. A medical imaging system comprising:
a scanner configured to continuously acquire image data sets of a volume of interest that includes a common region;
a four-dimensional (4D) processor configured to digitally combine reconstructed three-dimensional (3D) volume visualizations of the acquired image data sets to form 4D volume visualizations representing the 3D volume visualizations over a period of time, the 4D volume visualizations including first and second 4D volume visualizations, the first 4D volume visualization including an entirety of the common region during a first time period and the second 4D volume visualization including the entirety of the common region during a different second time period; and
a 4D viewer configured to display a modified 4D volume visualization of the entirety of the common region, wherein the 4D processor digitally combines the first and second 4D volume visualizations from the first and second time periods, respectively, by digitally subtracting the first 4D volume visualization of the first time period from the second 4D volume visualization of the second time period, the second time period being later than the first time period.

* * * * *

UNITED STATES PATENT AND TRADEMARK OFFICE
CERTIFICATE OF CORRECTION

PATENT NO. : 8,064,986 B2  
APPLICATION NO. : 11/286833  
DATED : November 22, 2011  
INVENTOR(S) : Profio et al.

Page 1 of 1

It is certified that error appears in the above-identified patent and that said Letters Patent is hereby corrected as shown below:

On the Title Page, in Field (74), under "Attorney, Agents, or Firm", in Column 2, Line 1, delete "Dean D. Smail;" and insert -- Dean D. Small; --, therefor.

In Column 9, Line 23, in Claim 13, after "first" insert -- time --.

Signed and Sealed this
Twenty-seventh Day of March, 2012

David J. Kappos
*Director of the United States Patent and Trademark Office*